United States Patent
Okamoto et al.

(10) Patent No.: US 9,115,044 B2
(45) Date of Patent: Aug. 25, 2015

(54) METHOD FOR PRODUCING TRANS-1-CHLORO-3,3,3-TRIFLUOROPROPENE

(71) Applicant: Central Glass Company, Limited, Ube-shi, Yamaguchi (JP)

(72) Inventors: Satoru Okamoto, Kawagoe (JP); Fuyuhiko Sakyu, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 14/359,441

(22) PCT Filed: Nov. 8, 2012

(86) PCT No.: PCT/JP2012/078927
§ 371 (c)(1),
(2) Date: May 20, 2014

(87) PCT Pub. No.: WO2013/077189
PCT Pub. Date: May 30, 2013

(65) Prior Publication Data
US 2014/0336424 A1 Nov. 13, 2014

(30) Foreign Application Priority Data
Nov. 21, 2011 (JP) .................................. 2011-253543

(51) Int. Cl.
*C07C 17/358* (2006.01)

(52) U.S. Cl.
CPC ........... *C07C 17/358* (2013.01); *C07B 2200/09* (2013.01)

(58) Field of Classification Search
CPC .......................... C07C 17/358; C07B 2200/09
USPC ......................................................... 570/151
See application file for complete search history.

(56) References Cited

U.S. PATENT DOCUMENTS

| | | |
|---|---|---|
| 5,600,037 A | 2/1997 | Cuzzato et al. |
| 6,018,084 A | 1/2000 | Nakada et al. |
| 8,704,017 B2 * | 4/2014 | Pokrovski et al. ............ 570/160 |
| 2010/0022809 A1 | 1/2010 | Cottrell et al. |
| 2010/0152504 A1 | 6/2010 | Hulse et al. |
| 2010/0256426 A1 | 10/2010 | Sakyu et al. |
| 2011/0201853 A1 * | 8/2011 | Tung et al. .................... 570/168 |
| 2011/0237844 A1 | 9/2011 | Tung et al. |
| 2012/0271069 A1 * | 10/2012 | Wang et al. ................... 570/151 |

FOREIGN PATENT DOCUMENTS

| | | |
|---|---|---|
| JP | 46-2579 | 1/1971 |
| JP | 6-128180 A | 5/1994 |
| JP | 9-183740 A | 7/1997 |
| JP | 11-180908 A | 7/1999 |
| JP | 2007-38216 A | 2/2007 |
| JP | 2009-91301 A | 4/2009 |
| JP | 2009-108049 A | 5/2009 |
| JP | 2010-528043 A | 8/2010 |
| TW | 175400 | 12/1991 |
| WO | WO 2005/014512 A2 | 2/2005 |
| WO | WO 2010/059496 A1 | 5/2010 |

OTHER PUBLICATIONS

Taiwanese Office Action dated Aug. 7, 2014 (four (4) pages).
International Search Report (PCT/ISA/210) dated Feb. 5, 2013, with English translation (Six (6) pages).

* cited by examiner

*Primary Examiner* — Shailendra Kumar
(74) *Attorney, Agent, or Firm* — Crowell & Moring LLP

(57) ABSTRACT

Provided is a method for producing trans-1-chloro-3,3,3-trifluoropropene usable as a raw material for a foaming agent for a hard polyurethane foam, a solvent, a cleaning agent, a cooling medium, a working fluid, a propellant, a fluorinated resin, etc., the method involving a step of bringing cis-1-chloro-3,3,3-trifluoropropene into contact with a catalyst, wherein the catalyst includes a fluorinated metal oxide or a metal fluoride each produced by applying a fluorination treatment to a metal oxide containing one kind or two or more kinds of metals and containing aluminum atoms that make up 50 at. % or more of metal atoms to thereby substitute some or all of oxygen atoms in the metal oxide with fluorine atom(s), wherein the fluorinated metal oxide or the metal fluoride is a compound produced through a drying treatment at 400 to 600° C.

10 Claims, No Drawings

METHOD FOR PRODUCING TRANS-1-CHLORO-3,3,3-TRIFLUOROPROPENE

This application is a 371 of PCT/JP2012/078927, filed on Nov. 8 2012.

TECHNICAL FIELD

The present invention relates to a method for producing trans-1-chloro-3,3,3-trifluoropropene.

BACKGROUND OF THE INVENTION

Trans-1-chloro-3,3,3-trifluoropropene (hereinafter, 1-chloro-3,3,3-trifluoropropene may be referred to as "1233zd" or merely as "1233") is useful as a raw material for a foaming agent for a hard polyurethane foam, a solvent, a cleaning agent, a cooling medium, a working fluid, a propellant, a fluorinated resin, etc. As an example of conventional techniques relating to the present invention, Patent Document 1 discloses a method for obtaining 1-chloro-3,3,3-trifluoropropene by reacting 1,1,1,3,3-pentachloropropane with hydrogen fluoride in the gas phase. Additionally, Patent Document 2 discloses a method of reacting 1,1,1,3,3-pentachloropropane with hydrogen fluoride in the absence of a catalyst thereby obtaining 1,1,1-trifluoro-3-chloro-2-propene (1-chloro-3,3,3-trifluoropropene). Furthermore, Patent Document 3 describes, as a method for producing 1-chloro-3,3,3-trifluoropropene, a process involving the step of causing a reaction of 1,1,1,3,3-pentachloropropane in a reactor vessel in the presence of a Lewis acid catalyst or a mixture containing a Lewis acid catalyst at a temperature of lower than 150° C. in the liquid phase, the step of continuously retrieving products in the reactor vessel (hydrogen chloride and 1-chloro-3,3,3-trifluoropropene) and the step of isolating 1-chloro-3,3,3-trifluoropropene obtained by the preceding step.

In the above-mentioned methods, however, 1-chloro-3,3,3-trifluoropropene is usually obtained in the form of a mixture of cis and trans isomers, which is disadvantageous when either one is put to use.

In view of the above, attempts had been made to interconvert them by isomerization; Patent Document 4 discloses a process of taking advantage of chemical equilibrium to transform trans-1-chloro-3,3,3-trifluoropropene into cis-1-chloro-3,3,3-trifluoropropene.

Additionally, Patent Document 5 mentions in Examples about isomerization of 1-chloro-3,3,3-trifluoropropene, in which when fluorinating trans-1-chloro-3,3,3-trifluoropropene to provide 1,1,1,3,3-pentafluoropropane there occurs isomerization reaction as a side reaction thereby producing cis-1-chloro-3,3,3-trifluoropropene.

Though isomerization reaction of Patent Document 4 was studied in the use of a fluorinated chromia oxide catalyst as a fluorinated catalyst, the yield of trans-1-chloro-3,3,3-trifluoropropene at reaction temperatures of 103-199° C. is low (58.9-70.2%). The product of Patent Document 5 is just a by-product. Accordingly, these methods are not always suitable for the industrially actual use.

REFERENCES ABOUT PRIOR ART

Patent Documents

Patent Document 1: Japanese Patent Application Publication No. 9-183740

Patent Document 2: Japanese Patent Application Publication No. 11-180908

Patent Document 3: International Application Publication No. 2005/014512

Patent Document 4: U.S. Patent Application Publication No. 2010/0152504

Patent Document 5: Japanese Patent Application Publication No. 2007-038216

SUMMARY OF THE INVENTION

Problems to be Solved by the Invention

Under the circumstances, a method for industrially advantageously and efficiently producing trans-1-chloro-3,3,3-trifluoropropene by isomerizing cis-1-chloro-3,3,3-trifluoropropene has been required.

Means for Solving the Problems

The present inventors eagerly made studies and resulted in a finding that cis-1-chloro-3,3,3-trifluoropropene represented by the following formula [1] can be isomerized to trans-1-chloro-3,3,3-trifluoropropene represented by the following formula [2] by being brought into contact with a certain catalyst which had been subjected to a drying treatment at a certain temperature. Furthermore, they found that the above-mentioned isomerization reaction can proceed at a temperature lower than that in the case of using other catalysts and that the target compound is gained with a high selectivity of about not less than 95%, thereby achieving the completion of the present invention.

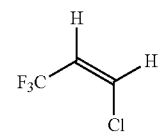

cis-1-chloro-3,3,3-trifluoropropene [1]

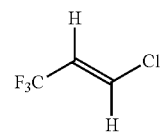

trans-1-chloro-3,3,3-trifluoropropene [2]

More specifically, the present invention involves [Invention 1] to [Invention 6] as follows, providing a method for producing trans-1-chloro-3, 3, 3-trifluoropropene.

[Invention 1]

A method for producing trans-1-chloro-3, 3, 3-trifluoropropene, comprising a step of bringing cis-1-chloro-3,3,3-trifluoropropene into contact with a catalyst, wherein the catalyst comprises a fluorinated metal oxide or a metal fluoride each produced by applying a fluorination treatment to a metal oxide comprising one kind or two or more kinds of metals and comprising aluminum atoms that make up 50 at. % or more of metal atoms to thereby substitute some or all of oxygen atoms in the metal oxide with fluorine atom(s), wherein the fluorinated metal oxide or the metal fluoride is a compound produced through a drying treatment at 400 to 600° C.

[Invention 2]

A method for producing trans-1-chloro-3,3,3-trifluoropropene, as discussed in Invention 1, wherein the catalyst comprises at least one kind of metal selected from the group consisting of chromium, titanium, manganese, iron, nickel, cobalt, magnesium, zirconium and antimony, in addition to the aluminum.

[Invention 3]

A method for producing trans-1-chloro-3,3,3-trifluoropropene, as discussed in Invention 1, wherein the fluorinated metal oxide or the metal fluoride is a fluorinated alumina or aluminum fluoride.

[Invention 4]

A method for producing trans-1-chloro-3,3,3-trifluoropropene, as discussed in any one of Inventions 1 to 3, wherein cis-1-chloro-3,3,3-trifluoropropene is brought into contact with the catalyst in the gas phase.

[Invention 5]

A method for producing trans-1-chloro-3,3,3-trifluoropropene, as discussed in any one of Inventions 1 to 4, wherein cis-1-chloro-3,3,3-trifluoropropene is brought into contact with the catalyst at 0 to 200° C.

[Invention 6]

A method for producing trans-1-chloro-3,3,3-trifluoropropene, as discussed in any one of Inventions 1 to 5, wherein cis-1-chloro-3,3,3-trifluoropropene is a mixture containing at least cis-1-chloro-3,3,3-trifluoropropene.

The applicant has disclosed a method of producing cis-1,2,3,3,3-pentafluoropropene comprising the step of bringing trans-1,2,3,3,3-pentafluoropropene into contact with a catalyst, wherein isomerization reaction can be developed with high selectivity and high yield by using an alumina catalyst that had been subjected to a fluorination treatment with hydrogen fluoride at 400-900° C. (Japanese Patent Application Publication No. 2009-91301). The applicant has further disclosed a method of producing trans-1,3,3,3-tetrafluoropropene comprising the step of bringing cis-1,3,3,3-tetrafluoropropene into contact with a catalyst (Japanese Patent Application Publication No. 2009-108049), wherein a metal oxide comprising one kind or two or more kinds of metals and comprising aluminum atoms that make up 50 at. % or more of metal atoms is extremely effective as the catalyst, and wherein the metal oxide subjected to a fluorination treatment at high temperatures of not lower than 200° C. is discussed as a preferable embodiment.

In view of the above, the present inventors had tried an isomerization reaction of cis-1-chloro-3,3,3-trifluoropropene (the starting material of the present invention) in the use of an alumina catalyst that had been subjected to a fluorination treatment as mentioned above; however, the reaction was hardly developed according to the temperature applied during the fluorination treatment. Even if the reaction was somewhat developed, the selectivity was inferior to the above-mentioned other compounds, so that this isomerization reaction could not be said to be satisfactory (see Reference Examples 1 and 2). As a reason therefor, it is assumed that steric hindrance that arises during isomerization due to chlorine atoms in cis-1-chloro-3,3,3-trifluoropropene is remarkable as compared with that arises from fluorine atoms in trans-1,2,3,3,3-pentafluoropropene or cis-1,3,3,3-tetrafluoropropene (see scheme 1).

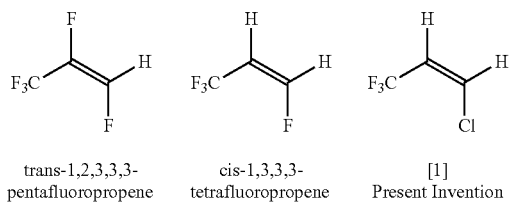

Scheme 1 trans-1,2,3,3,3-pentafluoropropene   cis-1,3,3,3-tetrafluoropropene   [1] Present Invention In the present invention, it was found that the isomerization reaction of cis-1-chloro-3,3,3-trifluoropropene proceeds with high selectivity, high yield and high efficiency if a drying treatment is conducted under a certain temperature condition on a catalyst that had undergone a fluorination treatment.

Effects of the Invention

According to the method of the present invention, it is possible to produce trans-1-chloro-3,3,3-trifluoropropene with higher selectivity and higher yield as compared with those achieved in conventional techniques. A catalyst to be used therein is manufacturable and available at very low cost. The present invention is greatly superior as a method for industrially producing trans-1-chloro-3,3,3-trifluoropropene.

MODE(S) FOR CARRYING OUT THE INVENTION

A method for producing trans-1-chloro-3,3,3-trifluoropropene, according to the present invention involves a step of bringing cis-1-chloro-3,3,3-trifluoropropene into contact with a metal catalyst (a contacting step) to cause isomerization, and characterized in that the metal catalyst comprises a fluorinated metal oxide or a metal fluoride each comprising one kind or two or more kinds of metals and comprising aluminum atoms that make up 50 at. % or more of metal atoms (hereinafter, the fluorinated metal oxide or the metal fluoride may be referred to generically as "a fluorinated metal oxide") and that the fluorinated metal oxide is a fluorinated metal oxide provided through a drying treatment at 400 to 600° C.

Incidentally, the scope of the present invention is not limited to the following explanations, and modifications and variations of the following examples will occur within a range not affecting the light of the invention. In addition, any publication cited in the specification of the present application e.g. prior art documents, patent documents such as patent publications is involved in the specification as references.

1. Contacting Step 1-1. Mode of Reaction

A contacting step is performed in the gas phase, and operation may be either a continuous type or a batch type. It is possible to suitably combine these reaction mode and operation types. Since chemical substances relating to the reaction have low boiling temperatures, an operation of a gas-phase continuous type is the most preferable in practical use. Though the gas-phase continuous operation accepts any of a fixed-bed type, a flow-bed type, a movable type and the like, the fixed-bed type is preferable because of its easiness and convenience.

1-2. Starting Material

A method for producing cis-1-chloro-3,3,3-trifluoropropene to be used in the present invention is not particularly limited and therefore it can be produced by a conventionally known method. For example, a method where 1,1,1,3,3-pentachloropropane is reacted with hydrogen fluoride in the gas phase thereby obtaining 1-chloro-3,3,3-trifluoropropene is known (Patent Document 1).

1-Chloro-3,3,3-trifluoropropene is gained in the form of a mixture of cis and trans isomers when produced by such methods, but in the production method according to the present invention it is possible to use the mixture as a starting material as it is, regardless of the ratio between cis and trans isomers. Even if the trans isomer is contained in a large amount or if the starting material is a mixture having an isomeric ratio between trans and cis isomers of trans:cis=90: 10, the content of trans isomer can be increased by the method of the present invention and therefore it is quite possible to use such a mixture as the starting material. On the other hand, 1-chloro-3,3,3-trifluoropropene consisting only of cis isomer is also usable.

1-Chloro-3,3,3-trifluoropropene obtained by the above-mentioned method of reacting 1,1,1,3,3-pentachloropropane with hydrogen fluoride in the gas phase or the other production methods is sometimes accompanied with side reaction products, hydrogen fluoride and the like. In the case of being accompanied with an acid component, it is required only to remove the acid component through a conventionally known method such as water cleaning.

Isomerization of cis-1-chloro-3,3,3-trifluoropropene into trans-1-chloro-3,3,3-trifluoropropene according to the present invention is achieved without purifying the other side reaction products.

In order to maintain the catalytic activity, 1-chloro-3,3,3-trifluoropropene as the starting material is preferably a dry treated one. The drying treatment can be achieved by using general-purpose drying agents such as a synthetic zeolite, silica gel, alumina and the like.

1-3. Product

The product obtained by the method of the present invention is not limited to a product substantially consisting only of trans-1-chloro-3,3,3-trifluoropropene, and required only to be a mixture where trans-1-chloro-3,3,3-trifluoropropene has an increased content relative to the content of cis-1-chloro-3, 3,3-trifluoropropene.

The product containing trans-1-chloro-3,3,3-trifluoropropene as the main component, obtained through the method of the present invention can be purified by a conventionally known method to be provided as a product.

The purification method is not limited but it is attainable by firstly rinsing the product with water or an alkaline aqueous solution to remove acidic substances such as hydrogen fluoride and then drying it, followed by distilling it so as to remove cis-1-chloro-3,3,3-trifluoropropene and organic impurities thereby obtaining trans-1-chloro-3,3,3-trifluoropropene, for example. The thus separated cis-1-chloro-3,3,3-trifluoropropene may be used again as the raw material for the isomerization reaction.

1-4. Reactor

The method of the present invention is carried out by using a reactor formed of a material substantially inactive against hydrogen fluoride and by introducing cis-1-chloro-3,3,3-trifluoropropene into a reaction zone filled with a temperature-adjusted catalyst. The vessel to be used ordinarily has the shape of a column and formed of stainless steel, Hastelloy™, Monel™, platinum, carbon, fluorocarbon polymers or a material having been subjected to lining with them.

1-5. Reaction Conditions

In the present invention, the temperature applied during a step of bringing cis-1-chloro-3,3,3-trifluoropropene into contact with a catalyst (a contacting step) is not particularly limited but preferably −10 to 300° C., more preferably 0 to 200° C., much more preferably 10 to 150° C. If the temperature during the contacting step is lower than −10° C., there arises the necessity to equip the reactor device with a special cooling facilities, which is not advantageous in view of energy efficiency and therefore not preferable. Meanwhile, the reaction rate is not particularly improved even if the temperature during the contacting step exceeds 300° C., or rather decomposition product is so formed as to reduce the selectivity of trans-1-chloro-3,3,3-trifluoropropene, which is not preferable.

In the present invention, cis-1-chloro-3,3,3-trifluoropropene to be supplied to the reaction zone may be supplied together with a gas not relating to the reaction, e.g. nitrogen, helium and argon. The ratio of the gas is not larger than 100 mol to 1 mol of the raw material consisting of cis-1-chloro-3,3,3-trifluoropropene or a mixture containing the same, preferably not larger than 10 mol. However, it is most preferable in ordinary cases that the above-mentioned gases are not used.

Pressure applied during the contacting step of the present invention is not particularly limited. Though the reaction is feasible without a particular pressure regulation (i.e., pressure application and pressure reduction), the pressure is preferably 0.01 to 1 MPa (absolute pressure) in terms of device. At the time of determining the pressure, it is preferable to select conditions where organic substances (e.g. the raw material) existing in the reaction system do not cause liquefaction in the reaction system.

The contact time during which cis-1-chloro-3,3,3-trifluoropropene and the catalyst are contacted in the contacting step of the present invention is normally 0.1 to 500 seconds, preferably 30 to 300 seconds in the standard state. A short contact time decreases the reaction efficiency and an excessively long contact time causes a side reaction, both of which are not preferable.

2. Catalyst

A fluorinated metal oxide to be used in the present invention is not particularly limited so long as it is a fluorinated metal oxide comprising one kind or two or more kinds of metals and comprising aluminum atoms that make up 50 at. % or more of metal atoms. However, from the viewpoint of availability and operational ease, the fluorinated metal oxide is preferably obtained by fluorinating a metal oxide that had been prepared as a catalyst.

2-1. Metal Oxide

A metal oxide is a metal oxide comprising one kind or two or more kinds of metals and comprising aluminum atoms that make up 50 at. % or more of metal atoms. As metal, it is possible to use aluminum alone, and additionally it is also possible to use a combination of aluminum and at least one kind of metal selected from the group consisting of chromium, titanium, manganese, iron, nickel, cobalt, magnesium, zirconium and antimony.

As a method for preparing the metal oxide, a conventionally known one can be employed. For example, the metal oxide can be prepared by: drying a sol of hydroxide obtained in such a manner as to neutralize a water-soluble salt of a metal compound with ammonia to precipitate it; pulverizing and molding the obtained aggregate; and calcining it. If a compound of a main metal is used in combination with a compound of at least one kind of metal different from the main metal, a multiple oxide can be prepared. Preferable examples of multiple oxide are those obtained between: alumina and chromium; alumina and zirconia; alumina and titania; and alumina and magnesia. These multiple oxides are required only to contain aluminum atoms that make up 50 at. % or more, preferably 80 at. % or more of metal atoms. When aluminum atoms is less than 50 at. %, the conversion rate in isomerization is unfavorably slow.

These metal oxides are commercially available in various types such as a catalyst and a drying agent, so that it is also possible to select from those types. These metal oxides may be used in the form of powder but usually in the form of granule. The shape and size thereof are not particularly limited and therefore determined according to the size of the reactor within the normal knowledge. Generally, it is preferable that the metal oxide is shaped into spheres, rods or tablets and has an average diameter or length of about 1 to 10 mm in view of ease of handling. The metal oxide sometimes takes one or more kinds of crystalline forms; for example, alumina includes crystalline forms of γ-alumina and α-alumina and titania includes crystalline forms of anatase and rutile. Though the crystalline form of the metal oxide may be any of the above, in the case of alumina it is preferable to use y-alumina which is large in surface area.

2-2. Fluorinated Metal Oxide

Preparation of a fluorinated metal oxide is performed by bringing the above-mentioned metal oxide into contact with a fluorination agent such as hydrogen fluoride, a fluorohydrocarbon, a fluorochlorohydrocarbon and the like (hereinafter referred to merely as "a fluorination treatment"). In ordinary cases, the fluorination treatment is preferably conducted step by step. When hydrogen fluoride is used, the fluorination treatment generates an intense heat, so that it is preferable that fluorination is firstly developed at relatively low temperatures by using a dilute hydrogen fluoride or a hydrogen fluoride gas and then developed at a gradually increasing concentration and/or temperature. The treatment at the final stage is preferably performed at a temperature of not smaller than the reaction temperature of isomerization reaction; however, in order to prevent the conversion with time during the reaction, it is further preferable to conduct fluorination at a temperature of not smaller than 150° C. or to conduct the fluorination treatment by using hydrogen fluoride at a hotspot temperature of not smaller than 250° C. The temperature does not particularly have the upper limit but a temperature exceeding 900° C. is difficult in terms of heat resistance of a fluorination treatment device, so that a temperature of not higher than 600° C. is practically preferable.

By conducting the fluorination treatment on the metal oxide, a fluorinated metal oxide some oxygen atoms of which are substituted with fluorine atom(s) or a metal fluoride all oxygen atoms of which are substituted with fluorine atoms is obtained, in which the ratio of the oxygen atoms being substituted with fluorine atoms is not particularly limited and therefore widely selectable.

Additionally, the fluorination treatment is preferably carried out before the use of the catalyst in order to prevent the variation of composition of the catalyst during the reaction.

3. Drying Treatment

The present invention is particularly characterized by conducting a drying treatment at a certain temperature on the catalyst that had been subjected to the fluorination treatment.

3-1. Drying Treatment

When applying the fluorination treatment to a metal oxide, the metal oxide is fluorinated and water is accessorily produced concurrently with the fluorination reaction. The accessorily produced water is assumed to be chemically adsorbed onto surface of the catalyst to inhibit the catalytic activity significantly. Hence in order to gain a high catalytic activity particularly at a low temperature and under a moderate reaction condition it is preferable to conduct a drying treatment at a high temperature on the catalyst before the catalyst comes into use for reaction. The drying treatment is preferably carried out by feeding an inert gas such as dry nitrogen gas, helium gas and the like, and the temperature is preferably 400 to 600° C., more preferably 450 to 550° C. A drying treatment of not lower than 600° C. increases the transition velocity of the crystal phase of the catalyst and therefore not preferable. If the drying treatment is performed in such a manner as to set the temperature of the final stage of the above-mentioned fluorination treatment within the same temperature region as the drying temperature (hereinafter such a treatment will be referred to as "a high temperature fluorination treatment"), a catalyst somewhat effective on the isomerization reaction can be obtained. However, the treatment takes much time because it is still necessary to continue the supply of hydrogen fluoride after the accessory production of water is terminated, and the selectivity in the isomerization reaction is inferior to that in a dry-treated one. It is therefore preferable to conduct the drying treatment from the viewpoint of reactivity, ease of operation etc.

Conditions for Treatment

The treatment time for the drying treatment depends on the treatment temperature and the kind and amount of the catalyst to be used. Consequently, the drying treatment can be determined according to conditions.

Any catalyst to be used in the present invention prefers the supply of chlorine, a fluorohydrocarbon, a fluorochlorohydrocarbon, a chlorohydrocarbon and the like into the reactor during the reaction, which is effective for elongating the lifetime of the catalyst and for improving the reaction rate and yield.

EXAMPLES

Referring now to Examples, the present invention will be discussed in detail; however, the present invention is not limited to those examples. A composition analysis value indicated by "%" means "an areal %" of a composition obtained by measuring the reaction mixture by gas chromatography (a detector is FID unless otherwise specified).

Catalyst Preparation Example 1

A reaction tube having a jacket was charged with 160 g of a granular γ-alumina (Sumika Alchem Co., Ltd., KHS-46) and heated to 150° C. Hydrogen fluoride was introduced thereinto at a flow rate of 15 g/h continuously until a hotspot reached an outlet of the reaction tube, thereby preparing a fluorinated alumina.

Comparative Example 1

A Case Where the Drying Treatment Was Not Performed

A gas-phase reactor (formed of SUS316L, having a diameter of 2.5 cm and a length of 40 cm) that consisted of a cylindrical reaction tube having an external heating device was charged with 50 ml of the catalyst prepared in Preparation Example 1 as a catalyst. Thereafter the temperature of the reaction tube was increased to 100° C. while feeding nitrogen gas at a flow rate of about 20 ml/m.

Subsequently, cis-1-chloro-3,3,3-trifluoropropene (including 99.5% of cis isomer) as a starting material was previously vaporized and then started to be fed into the reaction tube at a rate of about 0.10 g/m. The introduction of nitrogen gas was suspended at the time when the flow rate of organic substances was stabilized.

Since the reaction was stabilized after two hours after the initiation of the reaction, a gas discharged from the reactor was blown into water to remove an acidic gas, followed by analyzing the product by gas chromatography. The result is shown in Table 1.

Example 1

A Case Where the Drying Treatment Was Performed

In the same matter as in Comparative Example 1, the reaction tube was charged with the catalyst and increased in temperature to 500° C. while feeding nitrogen gas at a flow rate of about 500 ml/m. After the inner temperature of the reaction tube reached 450° C. or more, a drying treatment was carried out continuously for three hours.

After the termination of the drying treatment, the temperature of the reaction tube was decreased to 100° C. At the time when the temperature was stabilized, cis-1-chloro-3,3,3-trifluoropropene (including 99.5% of cis isomer) as a starting material was previously vaporized and then started to be fed into the reaction tube at a rate of about 0.10 g/m. The introduction of nitrogen gas was suspended at the time when the flow rate of organic substances was stabilized.

Since the reaction was stabilized after two hours after the initiation of the reaction, a gas discharged from the reactor was blown into water to remove an acidic gas, followed by analyzing the product by gas chromatography. The result is shown in Table 1.

Examples 2 to 4

A Case Where the Drying Treatment Was Performed

Reactions were performed in the same manner as in Example 1 with the exception that the reaction temperatures were 80° C., 60° C. and 45° C., respectively.

The results of Comparative Example and Examples are tabulated in Table 1.

TABLE 1

| | Treatment on Catalyst | Reaction Temperature (° C.) | Contact Time (s) | Composition (Areal %) | | Isomeric Ratio Trans/Cis |
|---|---|---|---|---|---|---|
| | | | | Trans-1233 | Cis-1233 | |
| | Raw Material | | | — | 99.52 | 0/100 |
| Comparative Example 1 | Not Dried | 100 | 188 | 0.01 | 99.45 | 0/100 |
| Example 1 | Dried at 500° C. | 100 | 184 | 94.85 | 4.68 | 95.3/4.7 |
| Example 2 | Dried at 500° C. | 80 | 184 | 95.9 | 3.87 | 96.1/3.9 |
| Example 3 | Dried at 500° C. | 60 | 188 | 96.56 | 3.16 | 96.8/3.2 |
| Example 4 | Dried at 500° C. | 45 | 192 | 96.79 | 2.91 | 97.1/2.9 |

As shown above, in the case where the catalyst that had not undergone the drying treatment was used for the reaction, an isomerization reaction of cis isomer into trans isomer was little confirmed (Comparative Example 1). On the contrary when the drying treatment had carried out at 500° C., the isomerization reaction of cis isomer into trans isomer was so greatly developed that the trans isomer was obtained with high selectivity (Examples 1 to 4). Additionally, the selectivity of trans isomer was further improved by making the reaction temperature lower (45° C.).

Reference Example 1

A Case Where the Catalyst Was Subjected to the Fluorination Treatment at 320° C.

In the same matter as in Comparative Example 1, the reaction tube was charged with the catalyst and increased in temperature to 320° C. while feeding nitrogen gas at a flow rate of about 20 ml/m. Hydrogen fluoride was introduced thereinto at a rate of about 0.3 to 0.4 g/m continuously for three hours to accomplish the fluorination treatment.

After the termination of the fluorination treatment, the temperature of the reaction tube was decreased to 100° C. At the time when the temperature was stabilized, cis-1-chloro-3,3,3-trifluoropropene (including 92.9% of cis isomer) as a starting material was previously vaporized and then started to be fed into the reaction tube at a rate of about 0.10 g/m. The introduction of nitrogen gas was suspended at the time when the flow rate of organic substances was stabilized.

Since the reaction was stabilized after two hours after the initiation of the reaction, a gas discharged from the reactor was blown into water to remove an acidic gas, followed by analyzing the product by gas chromatography. The result is shown in Table 2.

Reference Example 2

A Case Where the Catalyst Was Subjected to the Fluorination Treatment at 500° C.

A reaction was performed in the same manner as in Reference Example 1 with the exception that the temperature of the fluorination treatment was 500° C. The result is shown in Table 2.

TABLE 2

| | Treatment on Catalyst | Reaction Temperature (° C.) | Contact Time (s) | Composition (Areal %) | | Isomeric Ratio Trans/Cis |
|---|---|---|---|---|---|---|
| | | | | Trans-1233 | Cis-1233 | |
| | Raw Material | | | 0.06 | 92.85 | 0.1/99.9 |
| Reference Example 1 | Treated with HF at 320° C. | 100 | 156 | 0.15 | 92.73 | 0.2/99.8 |
| Reference Example 2 | Treated with HF at 500° C. | 100 | 161 | 80.21 | 12.06 | 86.9/13.1 |

As confirmed from Reference Example 1, the target isomerization reaction was hardly developed even at a fluorination treatment temperature of 320° C. When the fluorination treatment was conducted at a high temperature of about 500° C. as in Reference Example 2, the reaction proceeded excellently as compared with Reference Example 1 but a selectivity as much as that in the case of Example 1 where the catalyst had undergone the drying temperature at high temperatures was not obtained. With this, it is confirmed that the reaction according to the present invention can proceed far superiorly by applying the drying treatment to the catalyst.

Industrial Applicability

Trans-1-chloro-3,3,3-trifluoropropene obtained through the production method of the invention of the present application is useful as a raw material for a foaming agent for a

The invention claimed is:

1. A method for producing trans-1-chloro-3,3,3-trifluoropropene, comprising:
   a step of bringing cis-1-chloro-3,3,3-trifluoropropene into contact with a catalyst,
   wherein the catalyst comprises a fluorinated metal oxide or a metal fluoride each produced by applying a fluorination treatment to a metal oxide comprising one kind or two or more kinds of metals and comprising aluminum atoms that make up 50 at. % or more of metal atoms to thereby substitute some or all of oxygen atoms in the metal oxide with fluorine atom(s), wherein the fluorinated metal oxide or the metal fluoride is a compound produced through a drying treatment at 400 to 600° C.

2. A method for producing trans-1-chloro-3,3,3-trifluoropropene, as claimed in claim 1, wherein the catalyst comprises at least one kind of metal selected from the group consisting of chromium, titanium, manganese, iron, nickel, cobalt, magnesium, zirconium and antimony, in addition to the aluminum.

3. A method for producing trans-1-chloro-3,3,3-trifluoropropene, as claimed in claim 1, wherein the fluorinated metal oxide or the metal fluoride is a fluorinated alumina or aluminum fluoride.

4. A method for producing trans-1-chloro-3,3,3-trifluoropropene, as claimed in claim 1, wherein cis-1-chloro-3,3,3-trifluoropropene is brought into contact with the catalyst in the gas phase.

5. A method for producing trans-1-chloro-3,3,3-trifluoropropene, as claimed in claim 1, wherein cis-1-chloro-3,3,3-trifluoropropene is brought into contact with the catalyst at 0 to 200° C.

6. A method for producing trans-1-chloro-3,3,3-trifluoropropene, as claimed in claim 1, wherein cis-1-chloro-3,3,3-trifluoropropene is a mixture containing at least cis-1-chloro-3,3,3-trifluoropropene.

7. A method for producing trans-1-chloro-3,3,3-trifluoropropene, as claimed in claim 1, wherein the final stage of the fluorination treatment is performed at a temperature of not smaller than the reaction temperature of the isomerization reaction.

8. A method for producing trans-1-chloro-3,3,3-trifluoropropene, as claimed in claim 1, wherein the fluorination treatment is conduct at a temperature of not smaller than 150° C.

9. A method for producing trans-1-chloro-3,3,3-trifluoropropene, as claimed in claim 1, wherein the drying treatment is conducted on the catalyst before the catalyst comes into use for reaction.

10. A method for producing trans-1-chloro-3,3,3-trifluoropropene, as claimed in claim 1, wherein the drying treatment is performed within the same temperature region as that in the final stage of the fluorination treatment.

* * * * *